(12) United States Patent
Miles et al.

(10) Patent No.: US 6,866,759 B2
(45) Date of Patent: Mar. 15, 2005

(54) STEPPED ELECTROPHORESIS FOR MOVEMENT AND CONCENTRATION OF DNA

(75) Inventors: Robin R. Miles, Danville, CA (US); Amy Wei-Yun Wang, Oakland, CA (US); Raymond P. Mariella, Jr., Danville, CA (US)

(73) Assignee: The Regents of the University of California, Oakland, CA (US)

( * ) Notice: Subject to any disclaimer, the term of this patent is extended or adjusted under 35 U.S.C. 154(b) by 397 days.

(21) Appl. No.: 09/738,462

(22) Filed: Dec. 13, 2000

(65) Prior Publication Data

US 2002/0070113 A1 Jun. 13, 2002

(51) Int. Cl.⁷ ................... G01N 27/447; G01N 27/453
(52) U.S. Cl. ................ 204/457; 204/458; 204/608; 204/609; 204/451; 204/601; 204/643; 204/547; 435/6; 435/287.2
(58) Field of Search .................... 204/457, 458, 204/608, 609, 451, 601, 643, 547; 435/6, 287.2

(56) References Cited

U.S. PATENT DOCUMENTS

| 5,126,022 A | * | 6/1992 | Soane et al. ............... 204/458 |
|---|---|---|---|
| 5,376,252 A | | 12/1994 | Ekstrm et al. ............. 204/603 |
| 5,549,796 A | * | 8/1996 | Chu et al. .................. 204/457 |
| 5,645,702 A | * | 7/1997 | Witt et al. .................. 204/501 |
| 5,699,157 A | | 12/1997 | Parce ......................... 356/344 |
| 5,755,942 A | | 5/1998 | Zanzucchi et al. ......... 204/454 |
| 5,800,690 A | | 9/1998 | Chow et al. ................ 204/451 |
| 6,193,866 B1 | * | 2/2001 | Bader et al. ................ 204/450 |
| 6,319,472 B1 | * | 11/2001 | Ackley et al. ............. 422/68.1 |
| 6,685,812 B2 | * | 2/2004 | Miles .......................... 204/547 |
| 2002/0072054 A1 | * | 6/2002 | Miles et al. ................... 435/6 |
| 2002/0076690 A1 | * | 6/2002 | Miles et al. ................... 435/5 |
| 2002/0088712 A1 | * | 7/2002 | Miles et al. ................ 204/547 |
| 2002/0150886 A1 | * | 10/2002 | Miles et al. ................... 435/5 |
| 2003/0075444 A1 | * | 4/2003 | Huang et al. ............... 204/450 |

\* cited by examiner

*Primary Examiner*—Alan Diamond
(74) *Attorney, Agent, or Firm*—Eddie E. Scott; Alan H. Thompson; L. E. Carnahan

(57) ABSTRACT

A fluidic channel patterned with a series of thin-film electrodes makes it possible to move and concentrate DNA in a fluid passing through the fluidic channel. The DNA has an inherent negative charge and by applying a voltage between adjacent electrodes the DNA is caused to move. By using a series of electrodes, when one electrode voltage or charge is made negative with respect to adjacent electrodes, the DNA is repelled away from this electrode and attached to a positive charged electrode of the series. By sequentially making the next electrode of the series negative, the DNA can be moved to and concentrated over the remaining positive electrodes.

17 Claims, 2 Drawing Sheets

STEPPED ELECTROPHORESIS FOR MOVEMENT AND CONCENTRATION OF DNA

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to DNA assays particularly to the movement and concentration of DNA in microfluidic channels for assays such as amplification and hybridization, and more particularly to a stepped electrophoresis approach using a series of patterned electrodes for moving and concentrating the DNA in a microfluidic channel.

DNA is analyzed for many purposes from obtaining genetic information to identifying pathogens. The manipulation of DNA through microfluidic channels is useful in many assays such of DNA amplification and hybridization. Concentration of DNA at the input to an electrophoresis channel will yield a greater resolution for sequencing.

Electrophoretic channels currently have a single electrode at the input and at the output to move particles down the channels. The resolution of the electrophoretic device is highly dependent on the degree of concentration of the sample at the injection into the channel. Cross-channel injection is sometimes used to provide a small sample but this limits the amount of sample used and thus reduces the signal. Cross channel injection requires a second channel perpendicular to the separation channel and thus increases the amount of space (footprint) needed for injection.

DNA carries a negative charge and thus can be attracted to positively charged electrodes or repelled from negatively charged electrodes. Strong direct current (DC) fields in useful fluids such as water tend to breakdown due to electrolysis. Prior efforts have been directed to moving charged molecules through a medium by the application of a plurality of electric fields of sufficient strength and applied for sufficient amounts of time so as to move the charged molecules through the medium. Such prior approaches are exemplified by U.S. Pat. No. 5,126,022 issued Jun. 30, 1992 to D. S. Soane et al, and by U.S. Pat. No. 5,800,690 issued Sep. 1, 1998 to C. Y. H. Chow et al.

In the present invention a series of electrodes are placed along a fluidic channel and function to move DNA from electrode to electrode by placing a relatively small voltage (<10, preferably <2 between the electrodes. By applying the series of electrodes at the input to the microfluidic channel the sample can be moved sequentially from electrode to electrode to concentrate the sample at the end of the injection region. Thus, a high level of sample can be kept at a concentrated area to increase signal to noise of the device.

SUMMARY OF THE INVENTION

It is an object of the present invention to move and/or concentrate DNA in a microfluidic channel.

A further object of the invention is to concentrate a sample at the input to electrophoretic sequencing channels to increase the resolution of the electrophoretic devices.

A further object of the invention is to provide a method and apparatus using a series of charged electrodes or electrode segments to move DNA, such as in pathogen detection devices in counter biological warfare systems or for the use of DNA sequence and sample preparation for amplification and hybridization of DNA.

Another object of the invention is to provide a series of electrodes or electrodes with charged segments along a fluidic channel and move DNA from electrode to electrode by placing a relatively small (<10) voltage between the electrodes.

Another object of the invention is to concentrate a sample at the input of an electrophoretic separation channel by a patterned series of thin-film electrodes located adjacent to the injection region of the separation channel, and controlling the type of charge (positive or negative) applied to adjacent electrodes of the patterned series whereby the DNA is moved from electrode to electrode to enable concentration in the injection region.

Other objects and advantages of the present invention will become apparent from the following description and accompanying drawings. Basically, the present invention involves stepped electrophoresis for movement of and concentration of DNA. Since DNA carries a negative charge and thus can be attracted to positively charged electrodes or repelled from negatively charged electrodes, a series of electrodes along an injection region of a fluidic channel can move DNA from electrode to electrode and concentrate the DNA at the injection region by controlling the charge (positive or negative) on the adjacent electrodes of the series. The series of electrodes or electrodes with charged segments of this invention operate a relatively small voltage (<10V) between electrodes and thus do not cause breakdown by electrolysis of useful fluids such as water for transporting the DNA through the microfluidic channel. Since processing of DNA for amplification and hybridization requires movement and concentrate of the DNA at certain points, the series of electrodes may be formed at any desired point along the microfluidic channel and thus may be used for these applications. By the use of this invention, DNA can be moved in preference to positively charged or neutral species, and thus can be used to filter membrane or other cellular material from the DNA, as well as other background contaminants in the sample, such as salts, effectively cleaning the sample.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

The present invention involves stepped electrophoresis for movement and concentration of DNA. This is accomplished by applying a series of electrodes or electrodes with charged segments at the input of a fluidic microchannel so that the sample can be moved sequentially from electrode to electrode to concentrate the sample at the end of the injection region of the microchannel. Thus, one can keep a high level of sample but at a concentrated area to increase signal to noise of the device. Since DNA carries a negative charge and thus is attracted to positively charged electrodes or repelled from negatively charged electrodes, the charge on the series of electrodes along the fluidic microchannel can be changed so as to move DNA from electrode to electrode by placing a relatively small voltage (<10, preferably <2) between the electrodes. This small voltage is insufficient to breakdown of the sample fluid due to electrolysis.

Figure 1A:
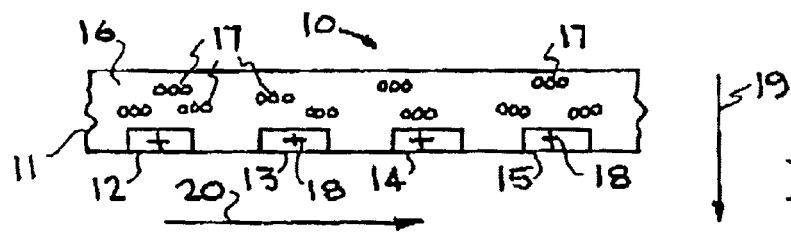
FIGS. 1A–1D schematically illustrates the movement and concentration of DNA by a series of properly charged electrodes in accordance with the present invention.
Figure 1B:
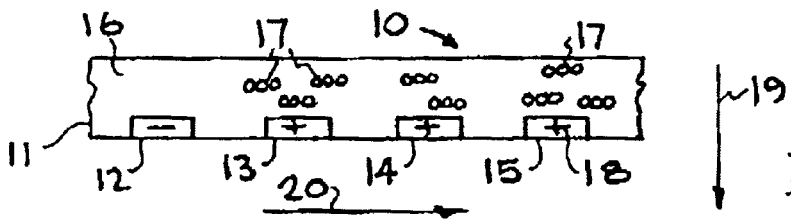
Figure 1C:
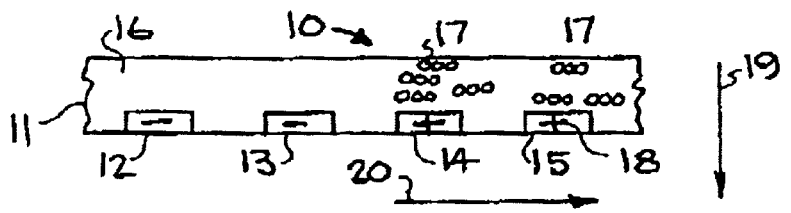
Figure 1D:
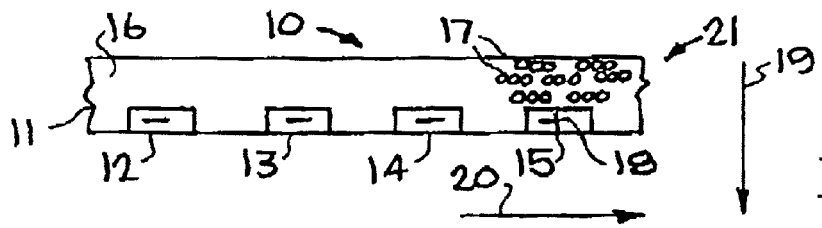
Figure 2:
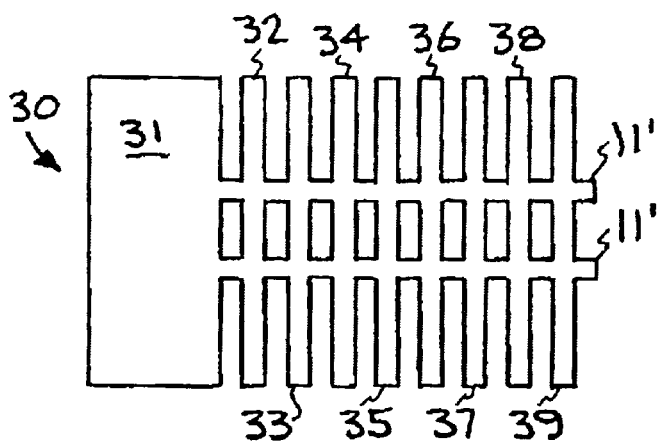
FIG. 2 illustrates a top view of a series of electrodes positioned at the injection region of a microfluid channel in accordance with the present invention.

FIGS. 1A–1B illustrate the invention and comprise a fluidic microchannel generally indicated at 10 having a channel wall 11 having patterned thereon a series of thin-film electrodes 12, 13, 14 and 15, each connected to a direct current (DC) power supply and charge switching apparatus. A greater number of electrodes may be utilized as seen in FIG. 2. As shown in FIG. 1A a channel fluid 16 containing DNA segments 17 injected at the input of the microchannel 10, with each of electrode 12–15 having a positive charge thereon, as indicated by arrow 18 to attract the DNA down to the electrodes. As the charge on the electrodes 12–15 is sequentially changed as illustrate in FIGS. 1B–1D over time as indicated by arrow 19, an arrow 20 indicates DNA movement so as to be concentrated adjacent electrode 15.

As seen in FIG. 1B the charge on electrode 12 is changed to negative thereby repelling the DNA 17 away from electrode 12, and attracted to the positive electrodes. As seen sequentially in FIGS. 1C and 1D, the charges on electrode 13 and 14 are changed to negative repelling the DNA 17 therefrom, whereby the DNA 17 is attracted to positively charged electrode 15 and is concentrated as indicated by arrow 21 adjacent positively charged electrode 15.

FIG. 2 is a top view of an embodiment of a series of electrodes patterned down into the input or injection section of an electrophoresis channel, such as shown in FIGS. 1A–1D. The electrode arrangement indicated generally at 30 includes a primary electrode 31 suspended in the solution at the end of the channel, and a patterned series of concentration electrodes indicated at 32, 33, 34, 35, 36, 37, 38 and 39. It is to be understood that another primary electrode, not shown, is located at the opposite end of the electrophoresis channel as known in the art. The two horizontal segments indicated at 11' between the electrodes constitute the outline of the microchannel 11. The number of concentration electrodes, four (12–15) in FIGS. 1A–1D or eight (32–39) in FIG. 2 is dependant on the desired amount of movement of an/or concentration of the DNA segments in the channel fluid.

While the embodiment illustrated in FIGS. 1A–1D and 2 show the series of electrodes being located at the input or injection region of the microchannel, a series of such patterned electrodes may be located anywhere along the length of the channel if such were desired to move or concentrate the DNA in the channel fluid.

Figure 3:
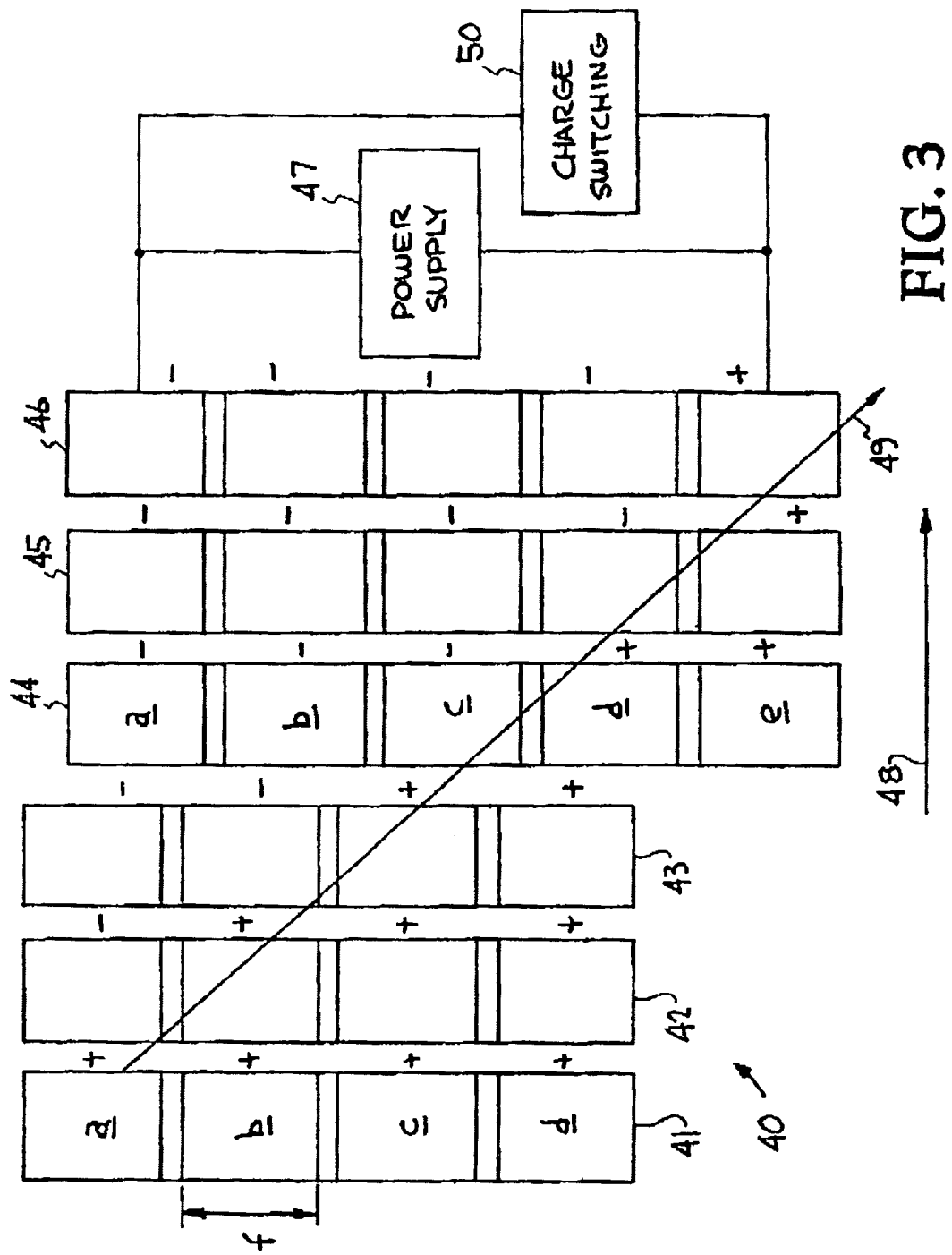
FIG. 3 illustrates the movement of DNA by the charged segment of a plurality electrode plates over a period of time using stepped electrophoretic movements with each charged segment being of a selected length, such as 50 μm.

FIG. 3 illustrates an embodiment of a series of segmented electrode plates and movement of a concentration of DNA in a channel fluid over time, with each electrode plate containing segments of which the charge thereon can be changed to repel or attract DNA segments in a channel fluid, as schematically illustrated in FIGS. 1A–1D. As shown the series of electrodes generally indicated at 40 comprises electrode plates 41, 42, 43, 44, 45 and 46 operatively connected to a DC power supply 47. Each electrode plate 41–43 includes four (4) charged segments a, b, c, d and electrodes 44–46 have 5 charged segments a, b, c, d, e, on which the charge is changed to cause DNA movement from or attraction toward the charged segment, each charged segment being indicated by a negative or positive charge placed therein and each charged segment has a length indicated by the arrow, f, of 50 μm, for example. Note that the charges on the charged segments of electrodes 41–43 is the same as the charges on electrodes 12–15 of FIGS. 1A–1C. Over time, indicated by arrow 48 the DNA is moved from electrode segment to electrode segment as indicated by arrow 49 so as to be concentrated adjacent electrode 46.

A charge switching apparatus, indicated generally at 50 in FIG. 3 is located intermediate the various electrodes, 12–15, 32–39 or electrodes segments a–d or a–f of electrodes 41–43 and 44–46 and the power supply, such as 47 in FIG. 3. The switching apparatus is basically a switching box in which the voltage applied to each electrode can be controlled and involves simple electronics and mechanical switches, known in the art.

It has thus been shown that the present invention provides stepped electrophoresis for movement and concentration of DNA. By the use of a series of electrodes or charged electrode segments and by selectively changing the charge on the electrodes or electrode segments DNA segments in a channel fluid can be moved and concentrated. In the illustrated embodiments the electrode series has been located adjacent the injection region of the microchannel, but could be located at other points along the length of the channel. The invention can be used to move DNA along microfluidic channels to concentrate the sample at the input to electrophoretic sequencing channels to increase the resolution of these devices. Also, the invention can be used to move DNA in pathogen detection devices, such as in counter biological warfare systems. In addition the invention can be used for DNA sequencing and sample preparation and cleanup for amplification and hybridization of DNA.

While particular embodiments, parameters, etc. have been described and illustrated to exemplify and teach the principles of the invention, such are not intended to be limiting. Modifications and changes may become apparent to those skilled in the art, and it is intended that the invention be limited only by the scope of the appended claims.

What is claimed is:

1. In an electrophoresis system for moving and concentrating DNA in a channel fluid, the improvement comprising:
   a series of electrodes located along a fluidic channel;
   each electrode of said series including a plurality of individually charged segments, and
   means for changing the electrical charge on at least certain of the adjacent electrodes by providing a voltage of <10V between said at least certain of the adjacent electrodes,
   whereby DNA is moved from electrode to electrode.

2. The improvement of claim 1, wherein said means includes a power supply for providing a voltage of <10V between at least certain of the adjacent electrodes.

3. The improvement of claim 1, wherein said series of electrodes are located adjacent an injection region of the fluidic channel.

4. The improvement of claim 1, wherein said means is operatively connected to said series of electrodes to change the electrical charge on the charged segments.

5. A stepped electrophoresis method for movement and concentration of DNA comprising:
   providing an electrophoretic channel,
   forming a series of electrodes along the channel to produce individually charged segments, said step of forming the series of electrodes includes forming each electrode in the series with said individually charged segments, applying a voltage of <10V between adjacent electrodes, directing a DNA containing fluid through the channel, and applying an electrical charge on the adjacent electrodes such that a negative charge repels the DNA and a positive charge attracts the DNA, and changing the electrical charge on at least certain of the electrodes such that DNA is moved and collected in an area around one of the electrodes.

6. The method of claim 5, wherein forming the series of electrodes is carried out so as to include patterning of the electrodes on a surface of the channel.

7. The method of claim 5, wherein forming the series of electrodes is carried out adjacent an input region of the channel.

8. The method of claim 5, wherein changing the electrical charge is carried out by changing an electrical charge on at least certain of said charged segments.

9. The method of claim 5, additionally including applying a voltage of less than 2 volts between adjacent electrodes in the series.

10. The method of claim 5, wherein forming the series of electrodes is carried out by forming at least four adjacent electrodes.

11. The method of claim 5, wherein forming the series of electrodes is carried out by forming at least four charged segments in each of a number of adjacent electrodes.

12. A stepped electrophoresis system including:

at least one electrophoretic microfluidic channel, a patterned series of electrodes positioned along the microfluidic channel, each electrode of said patterned series provided with a plurality of individually charged segments, a power supply for placing voltage of less than 10 volts between adjacent electrodes of the series, and means for changing an electrical charge on at least certain of the adjacent electrodes, wherein said means is operatively connected to change an electrical charge on at least certain of said charged segments.

13. The system of claim 12, wherein said patterned series of electrodes is located adjacent an input region of said microfluidic channels.

14. The system of claim 13, wherein each of said electrodes includes at least four charged segments.

15. The system of claim 12, wherein said patterned series of electrodes includes at least four electrodes.

16. The system of claim 12, wherein said means includes a charge switching apparatus.

17. The system of claim 12, wherein the voltage between adjacent electrodes of the series is less than 2 volts.

* * * * *